United States Patent [19]

Schliebs et al.

[11] 4,052,484
[45] Oct. 4, 1977

[54] SUBSTITUTED CYCLIC PHOSPHINE OXIDES

[75] Inventors: Reinhard Schliebs; Hans-Dieter Block, both of Cologne, Germany

[73] Assignee: Bayer Aktiengesellschaft, Leverkusen, Germany

[21] Appl. No.: 648,710

[22] Filed: Jan. 13, 1976

[30] Foreign Application Priority Data

Feb. 1, 1975 Germany .................. 2504333

[51] Int. Cl.² ................... C07F 9/32; C07F 9/48
[52] U.S. Cl. ................... 260/927 R; 204/158 HE; 252/437; 260/429.9; 260/440; 260/453 P; 260/501.14; 260/501.19; 260/502.4 P; 260/606.5 P; 260/606.5 F; 260/970
[58] Field of Search ........ 260/927 R, 501.14, 501.19, 260/502.4 P, 429.9, 440

[56] References Cited

U.S. PATENT DOCUMENTS 3,725,466  4/1973  Uhing ................. 260/927 R X

*Primary Examiner*—Richard L. Raymond
*Attorney, Agent, or Firm*—Burgess, Dinklage & Sprung

[57] ABSTRACT

A cyclic phosphine oxide of the formula

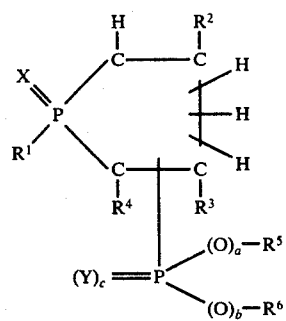

(I)

in which
R¹ is an alkyl or an aryl radical having up to 14 carbon atoms,
R², R³ and R⁴ each independently is a $C_1-C_4$-alkyl radical, hydrogen, chlorine or bromine,
X and Y each independently is oxygen or sulfur,
$a$, $b$, and $c$ each independently is 0 or 1, and
R⁵ is a $C_1-C_{12}$-alkyl radical and, where $a = 0$, also an aryl radical and, where $a = 1$, an equivalent of a cation,
R⁶ is a $C_1-C_{12}$-alkyl radical and, where $b = 0$, also an aryl radical and, where $b = 1$, an equivalent of a cation, is produced by reacting an unsaturated 5-membered cyclic phosphine oxide of the formula

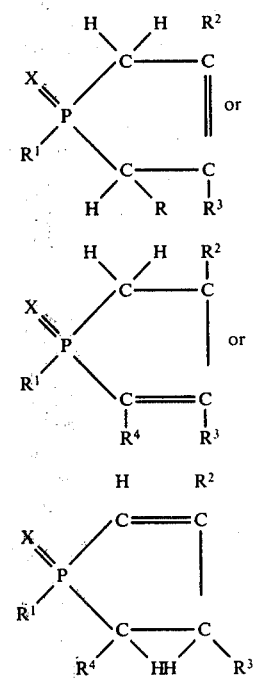

with a compound containing a phosphorus-hydrogen bond and of the formula

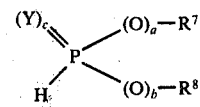

in which
R⁷ is a $C_1-C_{12}$-alkyl radical or, where $a = 0$, also an aryl radical, and
R⁸ is a $C_1-C_{12}$-alkyl radical or, where $b = 0$, also an aryl radical, in the presence of free radicals at a temperature of about 50° C to about 300° C, and the reaction product is optionally hydrolyzed and converted into a salt.

2 Claims, No Drawings

SUBSTITUTED CYCLIC PHOSPHINE OXIDES

This invention relates to new substituted cyclic phosphine oxides corresponding to the general formula (I):

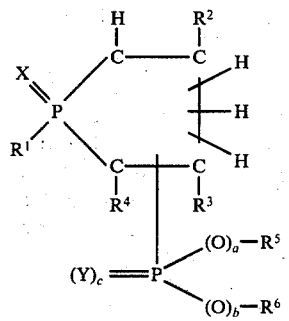

(I)

in which
- $R^1$ represents an alkyl or an aryl radical having up to 14 carbon atoms,
- $R^2$, $R^3$ and $R^4$ represent a $C_1$-$C_4$-alkyl radical, hydrogen, chlorine or bromine,
- $R^5$ represents a $C_1$-$C_{12}$-alkyl radical and, where $a = 0$, an aryl radical and, where $a = 1$, 1/n of an n-valent cation, such as a metal, ammonium, guanidinium, phosphonium or hydrogen,
- $R^6$ represents a $C_1$-$C_{12}$-alkyl radical and, where $b = 0$, an aryl radical and, where $b = 1$, 1/n of an n-valent cation such as, for example, a metal, ammonium, guanidinium, phosphonium or hydrogen,
- X and Y represent oxygen or sulfur, and
- $a$, $b$ and $c = 0$ or 1, and to a process for the production of these new compounds.

Among the tertiary phosphine oxides, those with a 4-membered or 5-membered saturated or unsaturated ring system, the so-called phosphetane or phospholine or phospholane ring systems, are distinguished by particularly high activity as catalysts in the formation of carbodiimides from isocyanates (cf. for example German Offenlegungsschrift No. 1,130,594).

The process for the production of the compounds according to the invention is distinguished by the fact that unsaturated 5-membered cyclic phosphine oxides corresponding to the general formulae:

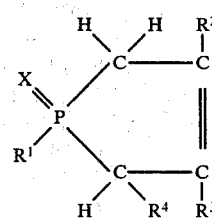

(II)

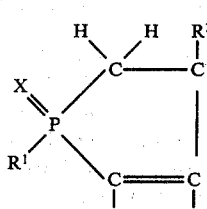

(IIIa)

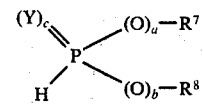

(IIIb)

in which $R^1$, $R^2$, $R^3$, $R^4$ and X have the same meaning as in formula (I), are reacted in the presence of free radicals at a temperature of about 50° C to about 300° C with a compound containing a phosphorus-hydrogen and of the formula

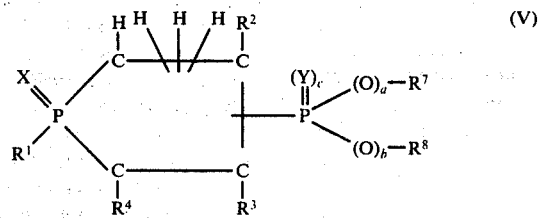

(IV)

in which $a$, $b$, $c$ and Y have the same meaning as in formula (I) and in which $R^7$ represents an alkyl radical or, where $a = 0$, also an aryl radical and $R^8$ represents an alkyl radical or, where $b = 0$, also an aryl radical, The primary products of formula (V):

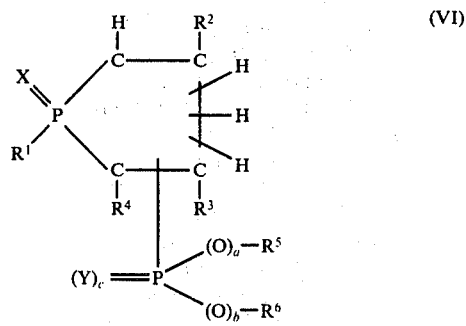

(V)

in which $R^1$, $R^2$, $R^3$, $R^4$, $R^7$, $R^8$, X, Y, $a$, $b$ and $c$ have the same meaning as in formulae (II), (III), and (IV), may be converted either by acid-catalyzed or by alkali catalyzed hydrolysis into the corresponding acids of the formula (VI)

(VI)

in which
$R^5$ represents hydrogen where $a = 1$, or $R^5 = R^7$ where $a = 0$, $R^6$ represents hydrogen where $b$ is 1, or $R^6 = R^8$ where $b = 0$, or into their salts and, when both $a$ and $b$ in formula (V) represent the number 1, into the acids corresponding to the formula (VII):

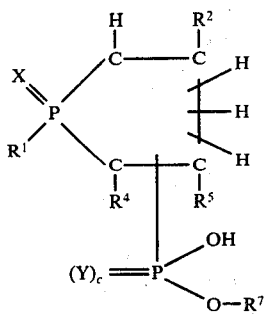

(VII)

or their salts. The aforementioned salts may of course also be obtained from the acids of formulae (VI) and (VII) by neutralization with monomeric or polymeric amines or other nitrogen-containing bases, with phosphines, ammonium, phosphonium or arsonium hydroxides, ammonium or phosphonium salts of weak acids with a $pK_s$-value of greater than 2, with metal oxides, metal hydroxides, metal salts of weak acids with a $pK_s$-value of greater than 2, and by reacting the acids of formulae (VI) and (VII) with base metals and by so-called double decomposition with metal salts or with monomeric or polymeric ammonium or phosphonium salts or the salts of other nitrogen-containing bases.

It has surprisingly been found that the phosphorus-hydrogen compounds of formula (IV) are added to the cyclic phosphine oxides of formulae (II) and (III), because the double bonds in the cyclic phosphine oxides (II) and (III) have proved to be sluggish with respect to radical polymerization and because there are also no terminal double bonds.

The starting materials for the process according to the invention corresponding to formulae (II) and (III) are known or may be obtained by known methods (cf. G.M. Kosolapoff, L. Maier, Organic Phosphorus Compounds, Wiley-Interscience, New York, 1972 et seq. vol 3, pages 370–371, pages 458–463 and vol 4, pages 9–10, page 48). The following are examples of 5-membered unsaturated phosphine oxides of this kind, whose double bonds may be situated either in the 2,3- or in the 3,4-position:

1-methyl-1-oxophospholine
1-ethyl-1-oxophospholine
1-butyl-1-oxophospholine
1-(2-ethylhexyl)-1-oxophospholine
1-methyl-1-thiophospholine
1-(2-chloroethyl)-1-oxophospholine
1-phenyl-1-oxophospholine
1-p-tolyl-1-oxophospholine
1-chloromethyl-1-oxophospholine
1,3-dimethyl-1-oxophospholine
1,2-dimethyl-1-oxophospholine
1-methyl-3-chloro-1-oxophospholine
1-methyl-3-bromo-1-oxophospholine
1-chlorophenyl-1-oxophospholine
1,3,4-trimethyl-1-oxophospholine
1,2,4-trimethyl-1-oxophospholine
1,2,2-trimethyl-1-oxophospholine
1-phenyl-1-thiophospholine
1-phenyl-3-methyl-1-oxophospholine
1-phenyl-2,3-dimethyl-1-oxophospholine The following compounds for example may be used as the phosphorus-hydrogen compounds in the process according to the invention:
dimethyl phosphite
diethyl phosphite
di-isopropyl phosphite
di-n-propyl phosphite
di-i-butyl phosphite
di-n-octyl phosphite
di-decyl phosphite
methyl-ethyl phosphite
methane phosphonous acid methyl ester
methane phosphonous acid ethyl ester
methane phosphonous acid-n-butyl ester
ethane phosphonous acid methyl ester
ethane phosphonous acid-2-ethylhexyl ester
benzene phosphonous acid methyl ester
benzene phosphonous acid-i-propyl ester
dimethyl phosphine oxide
methylethyl phosphine oxide
di-n-butyl phosphine oxide
methylphenyl phosphine oxide
diphenyl phosphine oxide
dimethyl thiophosphite
diethyl thiophosphite
di-i-butyl thiophosphite
methane thiophosphonous acid methyl ester
dimethyl phosphine sulfide
dimethyl phosphine
diethyl phosphine
diphenyl phosphine
methylphenyl phosphine
dibutoxy phosphine
methyl phosphine
ethyl phosphine
phenyl phosphine Suitable catalysts are the free radicals produced by radical formers active at temperatures in the range of from about 50° to 300° C which primarily belong to the groups of organic peroxides, aliphatic azo compounds and high-energy radiation, for example dialkyl peroxides, such as di-tert.-butyl peroxide; diacyl peroxides, such as dibenzoyl peroxide, p-chlorobenzoyl peroxide, 2,4-dichlorobenzoyl peroxide, succinyl peroxide, nonanoyl peroxide and lauroyl peroxide; peroxy esters, such as tert.-butyl peroctoate, tert.-butyl perisobutyrate, tert.-butyl peracetate, tert.-butyl perbenzoate, tert.-butyl perpivalate; and also peroxy ketals and percarbonates, azoisobutyronitrile, azo-bis-isobutanol diacetate, and also UV-rays, X-rays or γ-rays. Other equivalent radical formers are known among experts. Their suitability may readily be determined by simply preliminary tests.

The process according to the invention is generally carried out by adding the 5-membered unsaturated phosphine oxide dropwise to the phosphorus-hydrogen compound in a molar ratio of approximately 1:0.1 to 1:1. There is no need for a solvent, although if desired an inert solvent may be used. The radical former is used in a quantity of about 0.1 to 20 mole % and preferably in a quantity of about 0.5 to 5 mole %, based on the 5-membered unsaturated cyclic phosphine oxide, and is added with the latter to the reaction mixture. Before use, the radical former may be dissolved either in an inert solvent or in one of the reactants. It is also possible, however, optionally to mix the reactants with a small quantity of the radical former and subsequently to heat the mixture to the reaction temperature. Portions of radical formers, which have a sufficiently short half life at the reaction temperature, are then periodically added to the mixture at the reaction temperature.

The reaction temperatures are in the range of from about 50° to 300° C and preferably in the range of about 100° to 200° C. Depending upon the size of the reaction mixture and upon the reaction conditions, the reaction takes about 0.5 to 30 hours, i.e. the reaction time may be varied within wide limits.

The reaction is preferably carried out under normal pressure, although it may also be carried out under elevated or reduced pressure. The atmosphere under which the reaction is carried out may consist of air or an inert gas.

The reaction gives the products according to the invention in high yields. Unused starting materials may readily be recovered, for example by distillation. In general, the reaction products accumulate in the form of liquids after the excess starting materials have been distilled off. In some cases, these liquids may be further purified by distillation. According to analysis by spectroscopic methods, the reaction products are mixtures of stereoisomeric and positionally isomeric forms of compounds corresponding to formula (V).

The compounds according to the invention are valuable catalysts for the formation of carbodiimides from isocyanates. By comparison with catalysts of the kind normally used for carbodiimide formation, they enable activity to be strictly graduated by varying the substituents introduced by the process according to the invention.

In addition, they afford the possibility of producing catalysts for carbodiimide formation which are insoluble in the isocyanate-carbodiimide system. Thus, it is possible to produce low molecular weight carbodiimides from diisocyanates, polyisocyanates or mixtures of isocyanates differing in their functionality by separating off the catalyst insoluble in the system by simple operations, such as filtration or decantation, after a predetermined level of carbodiimide formation has been reached, thereby stopping carbodiimide formation at that level. In addition, the valuable and expensive catalyst may be recovered and repeatedly used.

The high volatility of the catalyst, which has frequently been found to give rise to difficulties in the production of monomeric carbodiimides from isocyanates by means of 1-methyl-1-oxophospholine, insofar as it can leave the end product with impurities after distillation, is either completely absent or present to only a very minimal extent in the substances according to the invention.

The ability of the compounds according to the invention to extract metal ions and metal salts, for example zinc chloride, from aqueous solutions, is superior to that of the phosphine oxides hitherto proposed for this purpose.

The process according to the invention is illustrated by the following Examples:

EXAMPLE 1

Production of 1-methyl-1-oxophospholane phosphonic acid dimethyl ester

A total of 117 g of an approximately 1:1-mixture of 1-methyl-1-oxophospholine-2 and 1-methyl-1-oxophospholine-3 is added dropwise with intensive stirring over a period of 1 hour at a temperature of 113° to 115° C to 550 g of dimethyl phosphite accommodated in a 1 liter glass flask. At the same time, a suspension of 8 g of dibenzoyl peroxide in silicone oil is added dropwise over the reaction time. All the materials used have been freed from traces of oxygen by repeated evacuation and venting with nitrogen.

On completion of the reaction, first the dimethyl phosphite and then the unreacted part of the 1-methyl-1-oxophospholine (81 g), which consists of substantially equal parts of the two isomers, are distilled off in vacuo. 28 g of an almost colorless oil (b.p. $_{0.5}$:185° to 190° C) distil over during distillation of the residue, thickening in the receiver into a white crystalline paste which becomes liquid again between 40° and 55° C.

Analysis: $C_7H_{16}O_4P_2$ calculated: 27.4%, P; 37.2% C; 7.1%, H. found: 28.0%, P; 36.8%, C; 7.0%, H.

According to analysis by gas chromatography, 4 different isomers are present.

EXAMPLE 2

Production of 1-methyl-1-oxophospholane phosphonic acid dimethyl ester 2900 g of 1-methyl-1-oxophospholine (isomer mixture as in Example 1) and 200 g of tert.-butyl peroctoate, dissolved in 750 ml of dimethyl phosphite, are added dropwise with stirring over a period of 4 hours at 110° to 115° C to 5500 g of dimethyl phosphite. The reaction takes place under a nitrogen atmosphere. Removal of the excess dimethyl phosphite and the unreacted phospholine oxide (170 g) by distillation leaves 5250 g of 1-methyl-1-oxophospholane phosphonic acid dimethyl ester (93% of the theoretical) as a residue which solidifies at 50° to 60° C.

Analysis: $C_7H_{16}O_4P_2$ calculated: 27.4% P; 37.2% C; 7.1% H. found: 27.2% P; 37.0% C; 7.0% H.

EXAMPLE 3

Production of 1-methyl-1-oxophospholane phosphonic acid diethyl ester 1380 g of diethyl phosphite are heated under nitrogen to 160° C. 348 g of 1-methyl-1-oxophospholine and 18 g of tert.-butyl peroxide are simultaneously added dropwise over a period of 2 hours at the above-mentioned temperature to the intensively stirred reaction mixture. Unreacted diethyl phosphite is distilled off in vacuo. The residue consists of a yellow liquid (775 g) which, according to analysis and the NMR-spectrum, has the constitution of a 1-methyl-1-oxophospholane phosphonic acid diethyl ester. The liquid can be distilled at 220° to 225°C/1 mm Hg with some slight decomposition.

Analysis: $C_9H_{20}O_4P_2$ calculated: 24.4% p; 42.5% C; 7.9% H. found: 24.2% P; 42.8% C; 7.8% H.

EXAMPLE 4

Production of 1-methyl-1-oxophospholane phosphonic acid diisopropyl ester 500 g of diisopropyl phosphite are heated to 110° C. 116 g of 1-methyl-1-oxophospholine and 6 g of tert.-butyl peroctoate in 30 ml of diisopropyl phosphite are simultaneously added over a period of 30 minutes under a nitrogen atmosphere to the thoroughly stirred reaction mixture. After removal of the unreacted starting materials by distillation, 248 g of 1-methyl-1-oxophospholane phosphonic acid diisopropyl ester are left in the form of a substantially colorless liquid which begins to decompose at a temperature above 160° C.

EXAMPLE 5

Production of 1-methyl-1-oxophospholane phosphonic acid di-i-butyl ester

A total of 116 g of 1-methyl-1-oxopholine and 6 g of tert.-butyl peroctoate in 30 ml of di-i-butyl phosphite are simultaneously added dropwise over a period of 30 minutes under nitrogen at 115° C to 582 g of diisobutyl phosphite. Removal of the unreacted starting materials by distillation leaves 270 g of a substantially colorless liquid which consists predominantly of 1-methyl-1-oxophospholane phosphonic acid di-i-butyl ester. For further purification, the product is dissolved in 300 ml of water, 3.9 g of sodium hydroxide are added, the solution is briefly heated to 70° C and, after testing for neutral reaction, is extracted 3 times with 100 ml of methylene chloride. Removal of the methylene chloride by distillation leaves 223 g of pure 1-methyl-1-oxophospholane phosphonic acid di-i-butyl ester.

EXAMPLE 6

770 g of dimethyl phosphite and 116 g of 1-methyl oxophospholine are mixed in a 1 liter flask, freed from oxygen by passing through a stream of nitrogen and heated to 90° C. 20 g of tert.-butyl peroctoate, dissolved in 80 ml of dimethyl phosphite, are added dropwise with stirring over a period of 10 hours. After another 15 hours at 90° C, dimethyl phosphite and 1-methyl-1-oxophospholine are distilled off. Distillation of the residue gives 146 g of 1-methyl-1-oxophospholane phosphonic acid dimethyl ester.

EXAMPLE 7

Production of 1-methyl-1-oxophospholanyl methyl phosphinic acid methyl ester

A total of 116 g of 1-methyl-1-oxophospholine and 6 g of tert.-butyl peroctoate in 30 g of methane phosphonous acid methyl ester are simultaneously added dropwise with stirring at 120° C to 282 g of oxygen-free methane phosphonous acid methyl ester. The reaction time is 90 minutes. Excess methane phosphonous acid methyl ester and a little 1-methyl oxophospholine are distilled off. For purification, the residue of 205 g of 1-methyl-1-oxophospholanyl methyl phosphinic acid methyl ester is distilled in vacuo (b.p. 210° –220° C) and gives 186 g of a pure product which hardens very slowly into star-shaped crystals which become liquid again at a temperature above 70° C.

EXAMPLE 8

Production of 1-methyl-1-thiophospholane phosphonic acid dimethyl ester 132 g of 1-methyl-1-thiophospholine are added dropwise under nitrogen over a period of 1 hour at a temperature of 115° to 120° C to 550 g of dimethyl phosphite. 1 g of tert.-butyl peroctoate in 40 ml of dimethyl phosphite is added dropwise over the same period. Excess dimethyl phosphite and part of the unreacted 1-methyl-1-thiophospholine are recovered by distillation at a sump temperature of up to 130°C/1 mm Hg. The residue (148 g) consists of 1-methyl-1-thiophospholane phosphonic acid dimethyl ester which is contaminated by approximately 10% of 1-methyl-1-thiophospholine. Dissolution in 500 ml of water, followed by extraction with 40 ml of trichlorethylene, gives an aqueous solution, free from 1-methyl-1-thiophospholine, from which 118 g of 1-methyl-1-thiophospholane phosphonic acid dimethyl ester can be re-extracted with chloroform.

EXAMPLE 9

Production of 1-methyl-1-oxophospholane thiophosphonic acid dimethyl ester 58 g of 1-methyl-1-oxophospholine and 3 g of tert.-butyl peroctoate in 5 ml of 1-methyl-1-oxophospholine are simultaneously added dropwise with stirring under nitrogen atmosphere to 132 g of dimethyl thiophosphite. The reaction temperature is 120° to 125° C. Removal of the dimethyl thiophosphite and a small quantity of 1-methyl-1-oxophospholine by distillation leaves 121 g of 1-methyl-1-oxophospholane thiophosphonic acid dimethyl ester which crystallizes on cooling. The colorless crystals become liquid again at a temperature above 80° C.

EXAMPLE 10

Production of 1-methyl-1-oxophospholanyl dimethyl phosphine oxide 116 g of 1-methyl-1-oxophospholine and 6 g of tert.-butyl perpivalate in dibutyl phthalate are added dropwise with stirring under an oxygen-free atmosphere to 234 g of dimethyl phosphine oxide. The reaction temperature is 75° to 80° C. The starting materials are then distilled off. The residue consists of 185 g of 1-methyl-1-oxophospholanyl dimethyl phosphine oxide.

EXAMPLE 11

Production of 1-methyl-1-oxophospholane phosphonic acid 226 g of 1-methyl-1-oxophospholane phosphonic acid dimethyl ester are heated for 3 days to boiling point with 500 g of water and 300 g of 36% hydrochloric acid. Methyl chloride and methanol distil off. After concentration by evaporation in vacuo, a total of 6 ml of product is taken up with 200 g of water and reconcentrated by evaporation. Thereafter no more chloride can be detected in the residue, and pure 1-methyl-1-oxophospholane phosphonic acid is left behind. Equivalent weight: found 98.2, calculated 99.

EXAMPLE 12

Production of the monosodium and disodium salts of 1-methyl-1-oxophospholane phosphonic acid The addition of 200 g of sodium hydroxide to 99 g of 1-methyl-1-oxophospholane phosphonic acid in 300 ml of water gives a solution with a pH-value of 5.3. Concentration of part of this solution by evaporation at 150°C/1 mm Hg gives the monosodium salt of 1-methyl-1-oxophospholane phosphonic acid in the form of a hygroscopic white crystalline substance having the composition: $C_5H_{11}O_4P_2Na \cdot 2H_2O$.

The addition of more sodium hydroxide to the residual solution up to pH 9.0 gives the disodium salt of 1-methyl-1-oxophospholane phosphonic acid which is obtained in pure crystalline form by concentrating the solution by evaporation at 100°C/1 mm Hg. Its composition corresponds to the formula $C_5H_{10}O_4P_2Na_2 \cdot 9H_2O$.

EXAMPLE 13

Production of the zinc salt of 1-methyl-1-oxophospholane phosphonic acid

A solution of 20 g of 1-methyl-1-oxophospholane phosphonic acid in 100 ml of water is poured over 13 g of zinc oxide. The zinc oxide is partly dissolved by thorough stirring for 1 hour. The undissolved fraction is filtered off and the solution is concentrated at 120°C/1 mm Hg, leaving behind white crystals of the zinc salt having the composition: $C_5H_{10}O_4P_2Zn.H_2O$.

EXAMPLE 14

Production of the monosodium salt of 1-methyl-1-oxophospholane phosphonic acid monomethyl ester 22.6 g of 1-methyl-1-oxophospholane phosphonic acid dimethyl ester in 100 ml of water are stirred with 4 g of sodium hydroxide for approximately 3 hours at room temperature and then for 10 minutes at 100° C. Thereafter less than 1% of the alkali used is still present. Concentration by evaporation at 200° C/1 mm Hg gives the monosodium salt of 1-methyl-1-oxophospholane phosphonic acid monomethyl ester in the form of a colorless, highly hygroscopic powder.

EXAMPLE 15

The neutralization of 22.6 g of 1-methyl-1-oxo-phospholane phosphonic acid with 10.5 g of diethanolamine gives the diethanol ammonium salt of 1-methyl-1-oxo-phospholane phosphonic acid in the form of a viscous oil.

EXAMPLE 16

200 ml of a so-called weakly basic anion exchanger in ball form (diameter 0.3 – 1.6 mm) based on polystyrene and containing dimethyl-amino groups, regenerated with sodium hydroxide, are treated in a column with 30 g of 1-methyl-1-oxophospholane phosphonic acid in 300 ml of water. The exchanger resin has a macroporous structure and a total capacity of 1.9 val/1. The resin charged with 1-methyl-1-oxophospholane phosphonic acid is washed with 3 liters of water and then dried in vacuo at 90° C. The dried exchanger resin contains approximately 30% by weight of 1-methyl-1-oxophospholane phosphonic acid. In contact with isocyanates, the resin thus prepared brings about the formation of carbodiimides.

EXAMPLE 17

When the procedure of Example 16 is repeated with 300 ml of a macroporous (>50% pore volume, 200-400 A pore diameter, 40-50 pore surface/g), strongly basic anion exchanger (ball form, diameter 0.3-1.5 mm) based on polystyrene with 5% divinylbenzene with a total capacity of 1.2 val/1, in which trimethyl ammonium ions are attached to the solid phase, a resin containing approximately 20% by weight of 1-methyl-1-oxophospholane phosphonic acid is obtained, showing similar activity with respect to isocyanates.

EXAMPLE 18

71 g of 1-methyl-1-oxophospholane phosphonic acid in the form of a 14% solution in water are added to 500 ml of strongly basic polystyrene-based exchanger resin regenerated with sodium hydroxide. The resin has a macroporous structure (ball form 0.3 –1.5 mm diameter) and a total capacity of 1.2 val/1 and contains dimethyl hydroxyethyl ammonium ions as anchor groups in the solid phase. After a contact time of 30 minutes, the charged resin is washed with 3 1-liter portions of water and the dried in vacuo. Approximately 30 g of 1-methyl-1-oxophospholane phosphonic acid are bonded per 100 g of dried resin.

EXAMPLE 19

500 ml of a medium-basic gel-form exchanger (ball form, diameter 0.3-1.2 mm) based on a polycondensation resin, which in addition to dimethylamine groups also contains trimethyl ammonium groups bonded to the solid phase, are regenerated with sodium hydroxide and washed with water until neutral.

The exchanger with a total capacity of 2.2 val/1 is brought into contact with 600 ml of an 18% aqueous 1-methyl-1-oxophospholane phosphonic acid solution containing 0.16 mole of hydrochloric acid. After a contact time of 2 hours, the aqueous phase is removed, the solid phase washed 4 times with 4 1-liter portions of water and then dried in vacuo. The dry preparation contains 36% of 1-methyl-1-oxophospholane phosphonic acid.

EXAMPLE 20

This Example shows the use of the compounds according to the instant invention:

a. Ionic fixation of the catalyst to insoluble matrices
200 ml of a so-called "weak-basic" commercial anion exchanger based on a polystyrene containing —N—(CH$_3$)$_2$-groups, which has been regenerated with sodium hydroxide solution, are treated in a column with 30 g of 1-methyl-1-oxophospholane phosponic acid in 300 ml of water. The exchanger resin has a macroporous structure and a total capacity of 1.9 val/1. When the resin has been laden with 1-methyl-1-oxophospholane phosphonic acid, it is washed with 3 1 of water and dried in a vacuum at 90° C. The dried exchanger resin contains approximately 30%, by weight, of 1-methyl-1-oxophospholane phosphonic acid.

b. Preparation of a catalyst consisting of a matrix and 1-methyl-1-oxophospholane phosphonic acid Approximately 30 parts, by weight, of 1-methyl-1-oxophospholane phosphonic acid are fixed to 70 parts, by weight, of a very strongly basic anion exchanger on a basic of polystyrene (5%, by weight, of divinyl benzene as cross-linking component) which has been prepared as described above and has a macroporous structure and contains —N$_\oplus$(CH$_3$)$_3$-anchoring groups. This matric has a pore volume of about 55%, a pore surface from 40 to 50 m$^2$ per gram of dry substance and an average pore diameter of from about 200 to 400 Angstrom units. The particle size is in the region of from 0.3 to 1.5 mm. The capacity of this matrix to swell in aliphatic poly-isocyanates is from about 30 to 40 vol.-%, measured by the increase in volume of the beads, and its capacity to swell in aromatic isocyanates, such as phenyl isocyanate or tolylene-2,4-diisocyanate, is from approximately 90 to 130 vol.-%. The matrix contains 2 $\times$ 10$^{18}$ basic goups per mg of dry substance.

The following demonstrates the surprising selectivity of such a catalyst described above (matrix on a basis of polystyrene with strongly basic anchoring groups):

500 parts, by weight, of 4,4'-diisocyanatodiphenyl methane (2 mol) and 34.8 parts, by weight, (0.2 mol) of a mixture of 80 parts, by weight, of tolylene-2,4-diisocyanate and 20 parts, by weight, of tolylene-2,6-diisocyanate are heated to 165° C for 35 minutes with 4 parts, by weight, of the above mentioned catalyst. Carbodiimidisation of the tolylene diisocyanate proceeds strictly selectively and a solution of about 7%, by weight, of the compound:

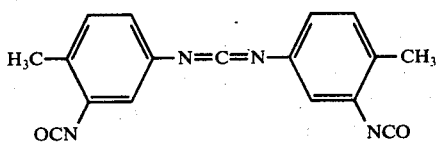

in 4,4-diisocyanatodiphenylmethane is obtained. This solution has the remarkably low viscosity of only about 68 cP/20° C and an isocyanate content of about 31.5%.

More than 70%, by weight, of the diisocyanato-carbodiimide formed is in equilibrium with a triisocyanato-uretone imine of the idealised formula:

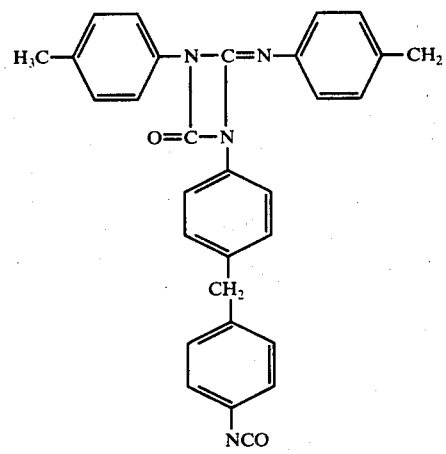

It is surprisingly found that even at concentrations of only about 7%, by weight, the diisocyanato-carbodiimide or its uretone imine triisocyanate is capable of liquefying 4,4'-diisocyanatodiphenylmethane which is crystalline at room temperature.

It will be appreciated that the instant specification and claims are set forth by way of illustration and not limitation, and that various modifications and changes may be made without departing from the spirit and scope of the present invention.

What is claimed is:
1. A cyclic phosphine oxide of the formula

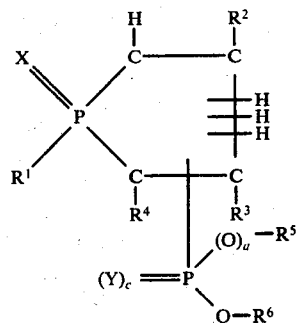

in which
R$^1$ is an alkyl or an aryl radical having up to 14 carbon atoms,
R$^2$, R$^3$ and R$^4$ each independently is a C$_1$-C$_4$-alkyl radical, hydrogen, chlorine or bromine,
X and Y each independently is oxygen or sulfur,
$a$ and $c$ each independently is 0 or 1, and
R$^5$ is a C$_1$-C$_{12}$-alkyl radical and, where $a = 0$, also an aryl radical and, where $a = 1$, also an equivalent of a cation,
R$^6$ is a C$_1$-C$_{12}$-alkyl radical.
2. A phosphine oxide according to claim 1, wherein $a = 1$ and R$^5$ is a C$_1$-C$_{12}$ alkyl radical or an equivalent of a cation selected from the group consisting of a metal, ammonium guanidinium, phosphonium and hydrogen ion.

* * * * *